(12) United States Patent
Dooney, Jr. et al.

(10) Patent No.: US 9,504,462 B2
(45) Date of Patent: Nov. 29, 2016

(54) SUTURE ANCHOR AND METHODS OF KNOTLESS TISSUE FIXATION

(71) Applicant: Arthrex, Inc., Naples, FL (US)

(72) Inventors: Thomas Dooney, Jr., Naples, FL (US); Alan M. Hirahara, Gold River, CA (US)

(73) Assignee: Arthrex, Inc., Naples, FL (US)

( * ) Notice: Subject to any disclaimer, the term of this patent is extended or adjusted under 35 U.S.C. 154(b) by 128 days.

(21) Appl. No.: 14/446,019

(22) Filed: Jul. 29, 2014

(65) Prior Publication Data

US 2015/0032157 A1  Jan. 29, 2015

Related U.S. Application Data (60) Provisional application No. 61/859,495, filed on Jul. 29, 2013.

(51) Int. Cl.
| | | |
|---|---|---|
| *A61B 17/04* | (2006.01) | |
| *A61B 17/06* | (2006.01) | |

(52) U.S. Cl.
CPC .... *A61B 17/0401* (2013.01); *A61B 2017/0406* (2013.01); *A61B 2017/0412* (2013.01); *A61B 2017/0445* (2013.01); *A61B 2017/0458* (2013.01); *A61B 2017/06185* (2013.01)

(58) Field of Classification Search
CPC ............... A61B 17/0401; A61B 2017/06185; A61B 2017/0458; A61B 17/0485; A61F 2/0811; A61F 2002/0852; A61F 2002/087; A61F 2002/0882

USPC ............................ 606/232; 623/13.13, 13.14
See application file for complete search history.

(56) References Cited

U.S. PATENT DOCUMENTS

| | | | |
|---|---|---|---|
| 7,875,058 B2 | 1/2011 | Holmes, Jr. | |
| 8,231,654 B2 | 7/2012 | Kaiser et al. | |
| 2007/0135843 A1* | 6/2007 | Burkhart | ........................ 606/232 |
| 2009/0312776 A1* | 12/2009 | Kaiser et al. | .................. 606/148 |
| 2010/0087857 A1 | 4/2010 | Stone et al. | |
| 2010/0268273 A1* | 10/2010 | Albertorio | ......... A61B 17/0401 |
| | | | 606/232 |
| 2011/0213416 A1* | 9/2011 | Kaiser | ........................... 606/232 |
| 2012/0123474 A1* | 5/2012 | Zajac et al. | .................... 606/232 |
| 2013/0144338 A1 | 6/2013 | Stone et al. | |
| 2013/0165972 A1* | 6/2013 | Sullivan | ............. A61B 17/0401 |
| | | | 606/232 |

FOREIGN PATENT DOCUMENTS

| | | |
|---|---|---|
| EP | 2 572 648 A1 | 3/2013 |
| EP | 2 601 894 A1 | 6/2013 |

* cited by examiner

*Primary Examiner* — Katherine M Shi
(74) *Attorney, Agent, or Firm* — Blank Rome LLP (57) ABSTRACT

Systems and methods for soft tissue to bone repairs, without knot tying. The soft tissue repair systems include self-cinching constructs with splices and loops having attached flexible materials that are pre-loaded onto modified knotless anchors (for example, swivel and/or screw-in suture anchors and/or push-in suture anchors with a distal eyelet) to position the self-locking, adjustable construct at the repair site. The systems allow for knotless tensioning of the tissue after the knotless anchors have been implanted.

11 Claims, 7 Drawing Sheets

SUTURE ANCHOR AND METHODS OF KNOTLESS TISSUE FIXATION

CROSS-REFERENCE TO RELATED APPLICATION

This application claims the benefit of U.S. Provisional Application No. 61/859,495 filed Jul. 29, 2013, the entire disclosure of which is incorporated by reference in its entirety herein.

FIELD OF THE INVENTION

The present invention relates to surgical devices and, in particular, to knotless suture constructs and associated methods of tissue repairs.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor or a hole provided in the bone tissue. Knotless suture anchors and knotless tensionable anchor constructs have been developed to facilitate tissue fixation to bone.

There is a need for knotless suture anchor constructs with improved design that allow tensioning of the tissue after implantation of the suture anchors. Also needed are improved technologies for knotless fixation of tissue with easier suture management and increased tensioning of the tissue.

SUMMARY OF THE INVENTION

The present invention fulfills the above needs and objectives by providing knotless, tensionable suture anchors and methods of tissue repair employing a knotless, tensionable suture anchor. The suture anchors of the present invention allow for tensioning after insertion in bone/tissue (to allow attached bone/tissue to be brought proximate to the bone/tissue) and do not require tying of any knots.

Other features and advantages of the present invention will become apparent from the following description of the invention.

DETAILED DESCRIPTION OF THE EMBODIMENTS

The present invention provides surgical constructs, systems and techniques for knotless tissue repair and fixation, such as fixation of a first tissue or substrate (for example, bone or soft tissue such as ligament, tendon, graft, etc.) to a second tissue or substrate (for example, bone or soft tissue such as ligament, tendon, graft, etc.). The present invention also provides improved knotless methods to fix tissue to bone, tissue to tissue, or bone to bone, using suture anchors.

The knotless suture constructs of the present invention use a mechanism similar to that of knotless SutureTak® but provide improvements in the design of the tensioning construct. Details of the formation of an exemplary knotless suture anchor employed in the embodiments of the present invention and with the splice-forming mechanism detailed below are set forth in U.S. Patent Publication No. 2013/0096611, entitled "Tensionable Knotless Anchors with Splice and Methods of Tissue Repair" and U.S. Patent Publication No. 2013/0165972, entitled "Tensionable Knotless Anchor Systems and Methods of Tissue Repair," the disclosures of both of which are incorporated by reference in their entirety herein.

The surgical constructs of the present invention comprise fixation devices (tensionable knotless anchors) provided with one or more flexible materials (a bunching suture/material) that allow the suture to go through the tissue (for example, soft tissue) and not around the tissue, and also to prevent the suture from return back through the tissue.

The surgical constructs comprise fixation devices (tensionable knotless anchors) that are inserted into bone with tensionable adjustable constructs attached to (pre-loaded onto) the fixation devices and that are self-cinching. As detailed below, a tensionable knotless construct is formed of a flexible strand provided with a splice formed within the strand, a spliced adjustable loop, a free end, and a flexible material attached to the spliced adjustable loop. The splice may be formed within the body or outside the body of the fixation device. Subsequent to the insertion of the fixation devices within the first tissue (and subsequent to passage of the flexible material attached to the spliced adjustable loop through a second tissue), the knotless self-locking mechanism of the tensionable construct allows the user (for example, the surgeon) to control the tension of the strand on the second tissue to be attached to the second tissue.

In an exemplary embodiment, a surgical construct comprises a fixation device (a suture anchor) with an attached (pre-loaded) tensionable construct formed of a flexible strand with a free end, a spliced adjustable loop (located within the body of the fixation device), a knotted fixed end or insert molded fixed end, and a flexible material (a suture/strand/bunching material) attached to the spliced adjustable loop to allow passage of the construct through tissue in only one direction. The knotted end (fixed end) is located on the fixation device (suture anchor), allowing the splice to be contained within the anchor body. The flexible material is attached to the loop before the formation of the spliced adjustable loop, or after the formation of the spliced adjustable loop.

The present invention also provides methods of tissue repair (for example, soft tissue to bone repair) which do not require tying of knots and allow adjustment of both the tension of the suture and the location of a first tissue with respect to a second tissue. An exemplary method of the present invention comprises inter alia the steps of (i) providing a surgical construct comprising a fixation device (for example, an anchor) with an adjustable, tensionable construct attached to (pre-loaded onto) the fixation device, the knotless tensionable construct including a flexible strand with a splice, a spliced adjustable loop, a free end, and a flexible material attached to the spliced adjustable loop; (ii) inserting the fixation device with the attached (pre-loaded)

knotless tensionable construct at a first location into a first tissue (for example, bone or soft tissue); (iii) passing the flexible material attached to the spliced adjustable loop through a second tissue (for example, soft tissue); and (iv) pulling on the free end to tension the final construct and adjust the distance between the first and second tissues.

Another exemplary method of the present invention comprises inter alia the steps of: (i) providing a surgical construct comprising a fixation device (for example, an anchor) with an adjustable, tensionable construct attached to (pre-loaded onto) the fixation device, the knotless tensionable construct including a flexible strand with a splice formed within the flexible strand, a spliced adjustable loop, a free end, a fixed end in the form of a knot, and a flexible material (suture/strand/bunching material) attached to the spliced adjustable loop; (ii) inserting the fixation device with the attached (pre-loaded) knotless tensionable construct into a first tissue (for example, bone or soft tissue); (iii) passing the flexible material attached to the spliced adjustable loop through a second tissue to be fixated (or reattached) to the first tissue; and (iv) subsequently, pulling on the free end of the flexible strand to allow the flexible material to bunch up on a surface of the second tissue, and to allow the second tissue to achieve the desired location relative to the first tissue upon tensioning of the final construct.

Another exemplary method of the present invention comprises inter alia the steps of: (i) providing a surgical construct comprising a fixation device (for example, an anchor) pre-loaded with a tensionable construct, the tensionable construct being self-cinching consisting of a flexible strand (for example, suture) extending through the body of the fixation device, the flexible strand consisting of a free end, a knotted fixed end or an insert molded fixed end, and a splice with a spliced adjustable loop, the splice being located within the body of the fixation device and the loop having an adjustable length/perimeter, the spliced adjustable loop of the tensionable construct being pre-built with an additional flexible material attached to the spliced adjustable loop, the flexible material being configured to bunch up upon tensioning of the tensionable construct; (ii) inserting the fixation device into a first tissue; (iii) passing the flexible strand with the flexible material through a second tissue to be fixated (or reattached) to the first tissue so that the flexible material passes through the second tissue in only one direction and is positioned on a surface of the second tissue; and (iv) pulling on the free end to decrease the perimeter of the spliced adjustable loop and to cause the flexible material to bunch up on the surface of the second tissue, and to further cause the second tissue to contact the first tissue.

The flexible strand of the knotless tensionable construct may be passed through at least a portion of the body of the fixation device (for example, through a full cannulation of the fixation device, or through a transversal opening at a distal end of the fixation device). Alternatively, the flexible strand may be fixed to the fixation device (which may be solid or cannulated) by overmolding the suture to the anchor body or by compressing the suture against the bone (achieving an interference fit between the fixation device and the bone tunnel, compressing the flexible strand). The splice may be formed within the body of the fixation device or outside the body of the fixation device. Upon insertion into the first tissue (for example, bone) and tensioning, the splice may reside within the body of the fixation device or outside the body of the fixation device.

In an exemplary embodiment only, the fixation device is a suture anchor (for example, a 5.5 mm Arthrex Corkscrew® anchor, disclosed in U.S. Pat. No. 6,117,162) modified to carry a suture that is spliced in a manner similar to an Arthrex ACL TightRope®, such as disclosed in U.S. Pat. Nos. 8,439,976 and 8,460,379, the disclosures of which are incorporated in their entirety by reference herein. The tensionable suture is free with a fixed end (that may be looped or knotted, for example). Once the suture anchor (the modified 5.5 mm Corkscrew® anchor) has been implanted, the driver is removed and the suture bundle with the attached bunching material is exposed. The suture bundle is then passed through the second tissue (for example, the rotator cuff) in only one direction, and tensioning of the construct may then be conducted to cause the bunching material to bunch up and to allow the second tissue (rotator cuff) to be positioned relative to the first tissue (bone), i.e., to be brought adjacent and/or in contact with the first tissue.

Once the sutures are tightened by pulling the free ends for tensioning, the ends are then clipped and the steps may be repeated for a second (or multiple) repair.

Reference is now made to FIGS. 1-7 which illustrate suture anchor construct 100 (reconstruction system 100) of the present invention employed in exemplary methods of attaching a first tissue (first substrate) to a second tissue (second substrate).

Figure 1:
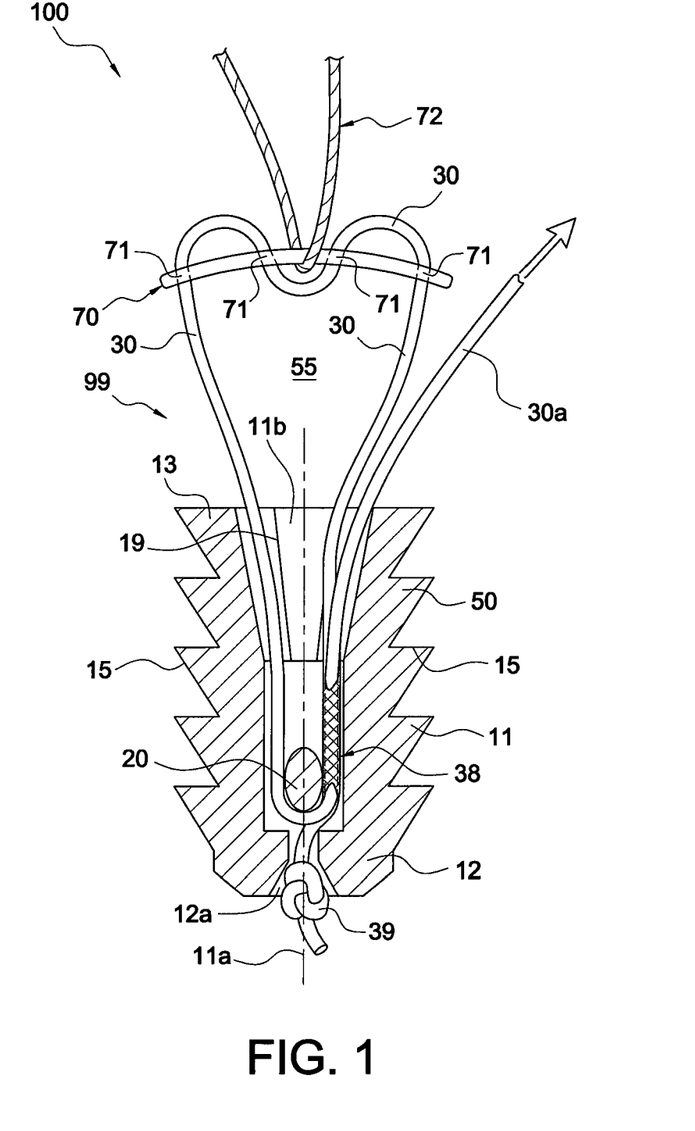
FIG. 1 illustrates an exemplary embodiment of a tensionable knotless anchor construct of the present invention.

The tensionable knotless anchor construct 100 shown in FIG. 1 is formed of anchor 50 provided/loaded with tensionable construct 99 formed of suture 30 forming a knotless, adjustable self-cinching loop 55 (knotless self-locking mechanism) and with flexible material 70 securely attached to suture 30. As detailed below, flexible material 70 may be any bunching material in the form of a piece of suture, suture tape, suture chain, woven material, textile, mesh, netting, etc., or any combination of these materials that allow the flexible material to fold and pass through tissue, in only one direction, and then bunch up or accordionize when the construct is tensioned. The flexible material 70 is slidingly attached to the flexible strand 30 (flexible cord 30) by passing the flexible strand 30 through different points spaced apart a length of the flexible material 70, beginning with a first point and then passing the flexible strand through another, second point (at a position adjacent the first point) to form a loop. When the flexible strand 30 is pulled, the loop between the two points collapses (is decreased) and the flexible material 70 compresses from an extended, non-folded position to a compressed, folded position. In the compressed position, the flexible material 70 may be compressed to form a plurality of folds in the shape of an accordion, for example. One or more flexible materials may be provided slidingly attached to the flexible strand 30.

Anchor 50 has an anchor body 11 which is solid and provided with a longitudinal axis 11a, a proximal end 13 and a distal end 12, and a plurality of ribs 15 extending circumferentially around it. Cannulation 11b extends along the body 11 to allow passage of flexible strand 30 (and of any suture passing devices attached to strand 30) to pass around post 20. Static knot 39 prevents suture 30 from passing through distal blind hole 12a.

Details on the formation of knotless, adjustable self-cinching loop 55 with splice 38 (cinching mechanism 38) are set forth in U.S. Patent Publication No. 2013/0096611, entitled "Tensionable Knotless Anchors with Splice and Methods of Tissue Repair," the disclosure of which is incorporated by reference in its entirety herein. During the formation of the knotless, adjustable self-cinching loop 55, suture 30 is pulled towards tensionable knotless anchor 50 (while pulling on a suture passing device such as a FiberLink™ or a nitinol loop) so that the suture doubles on itself inside the body of the tensionable knotless anchor. By further pulling on the suture passing device through the splice region 38 of suture 30, a splice is formed within the strand 30 and within the body of the anchor 50.

FIG. 1 also illustrates knotless anchor construct 100 provided with flexible material 70 attached to flexible strand 30. Flexible material 70 (bunching suture/material 70) may include any material (or combination of materials) that may be natural or synthetic, absorbable or resorbable, and may have any shape/geometry that allows it to be attached to flexible strand 30 and yet to bunch up once tensioning of the knotless anchor occurs after the anchor is secured into a substrate (for example, into a hole/socket/tunnel formed in the bone, or into soft tissue) by using a driver. Flexible material 70 can be any soft, hard or biologic material. It can either bunch up (like suture) or turn over the tissue (like an oblong button) to prevent pulling back through the bone/tissue. As detailed below, flexible material 70 provides one-way passage of the flexible strand 30 through a second tissue which is different from a first tissue (wherein the fixation device 50 is installed).

The flexible material 70 may have various forms and geometries (for example, rectangular or square, among many others) that allow flexible strand 30 to attach thereto (either in a fixed or modular manner). In an exemplary-only embodiment, the flexible material 70 of the constructs of the present invention may be formed of suture tape such as FiberTape® (disclosed in U.S. Pat. No. 7,892,256). Preferably, the flexible material 70 includes a flexible material which may be non-absorbable, absorbable or resorbable, and which allows passing of at least one flexible strand (such as strand 30) through at least a portion of the flexible material (for example, through at least a length of the flexible material).

In an exemplary-only embodiment, the flexible material 70 (bunching suture/material 70) material is provided as a rectangular material piece having a plurality of attachment points 71 (for example, eyelets) to allow the flexible strand 30 to pass therethrough. The attachment points 71 may be have various forms and configurations (for example, apertures, eyelets, openings) and may be located at various locations on the flexible material 70 (i.e., relative to the length of the bunching suture/material 70) to allow easy passage of strand 30 through the attachment points 71.

As detailed below, subsequent to the insertion of the anchor construct 100 into a first tissue (first substrate), a passing suture 72 (FIG. 1) is attached to or with flexible material 70, and the flexible material 70 is folded and subsequently passed through a second tissue (second substrate) by pulling on the passing suture 72 in a first direction. Pulling on the free end 30*a* of the flexible strand 30 to tension the construct in a second direction different from the first direction allows the flexible material 70 to bunch up and stop at the second tissue.

The present invention also provides methods of tissue repair which do not require tying of knots and allow adjustment of both the tension of the suture and the location of a first tissue (first substrate) with respect to a second tissue (second substrate).

Figure 2:
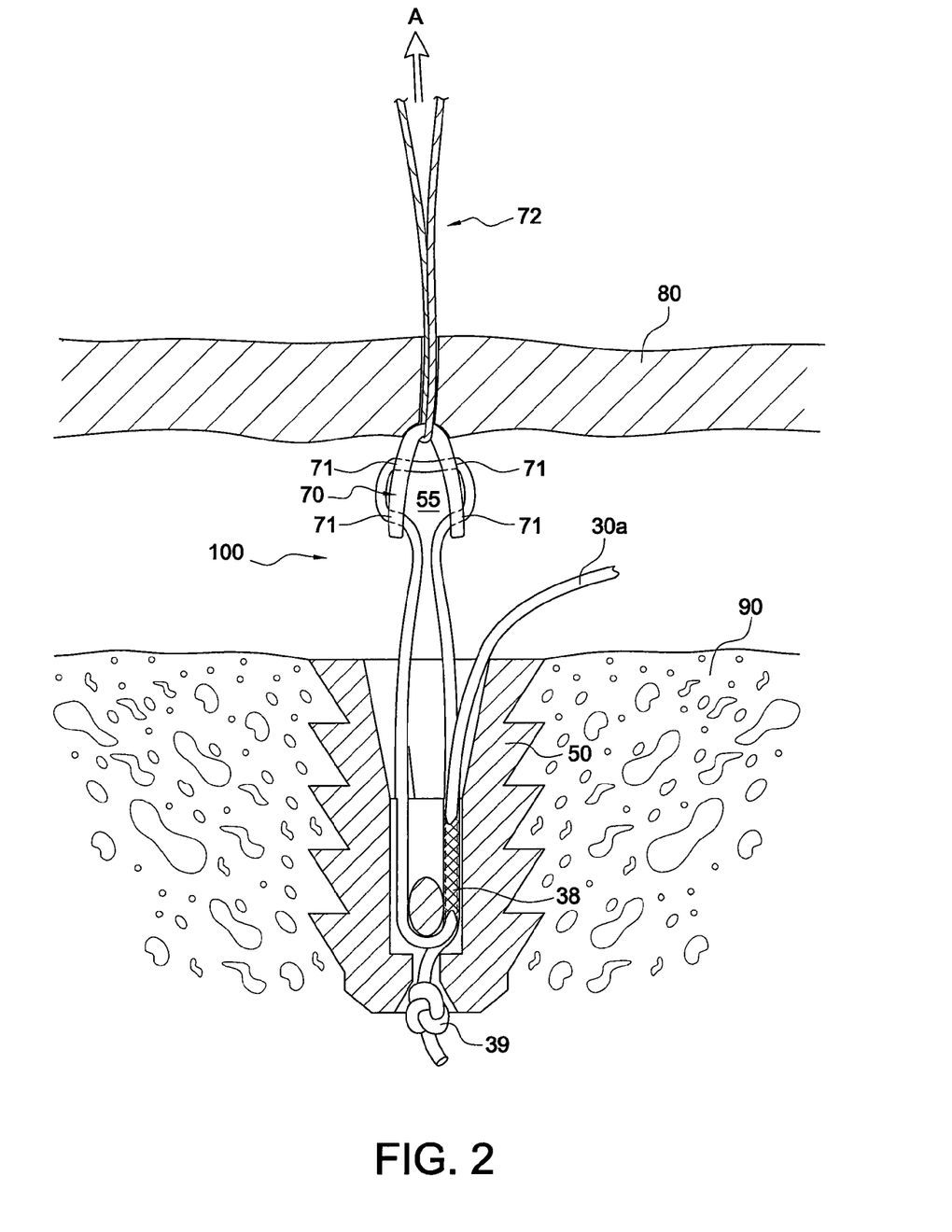
FIGS. 2-5 illustrate subsequent steps of a method of tissue repair using a tensionable knotless anchor construct according to an exemplary embodiment of the present invention (insertion method 1).

Reference is now made to FIGS. 2-5 which illustrate subsequent steps of an exemplary method of tissue fixation with suture anchor construct 100 (reconstruction system 100) of the present invention. The suture anchor construct 100 is inserted and secured into a first tissue 90 (first substrate 90), which may be bone or soft tissue, as shown in FIG. 2. A passing suture 72 is attached to the flexible material 70 and then passed through a second tissue 80 (second substrate 80), which may be bone or soft tissue. As the passing suture 72 is pulled through the second tissue 80 (bone/soft tissue 80) in the direction of arrow A (FIG. 2), the flexible material 70 folds down to pass through the second tissue 80.

Figure 3:
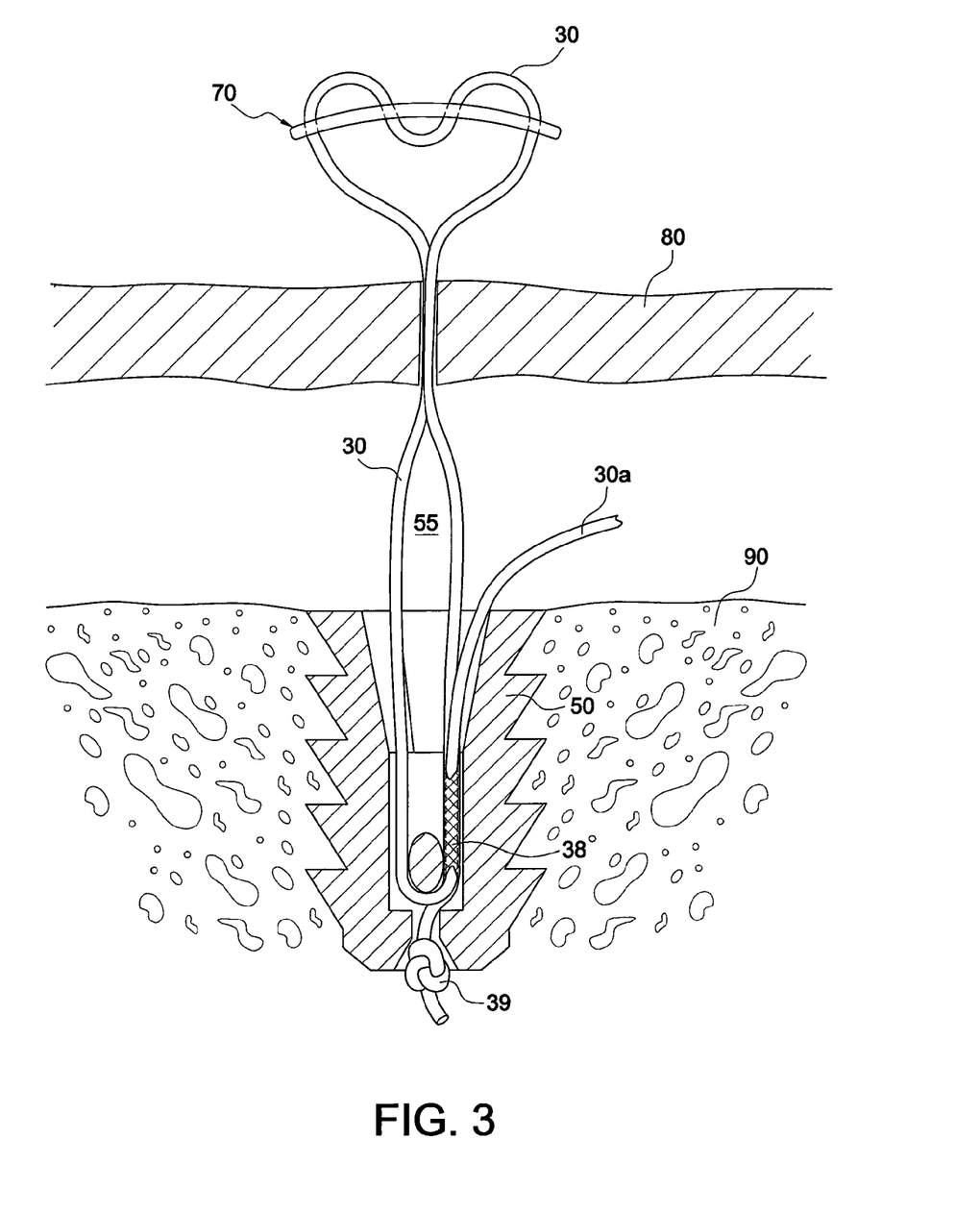

FIG. 3 shows the passing suture 72 removed from the anchor construct 100 and the flexible material 70 passed through the second tissue 80 (bone/tissue 80). The construct is ready for tensioning.

Figure 4:
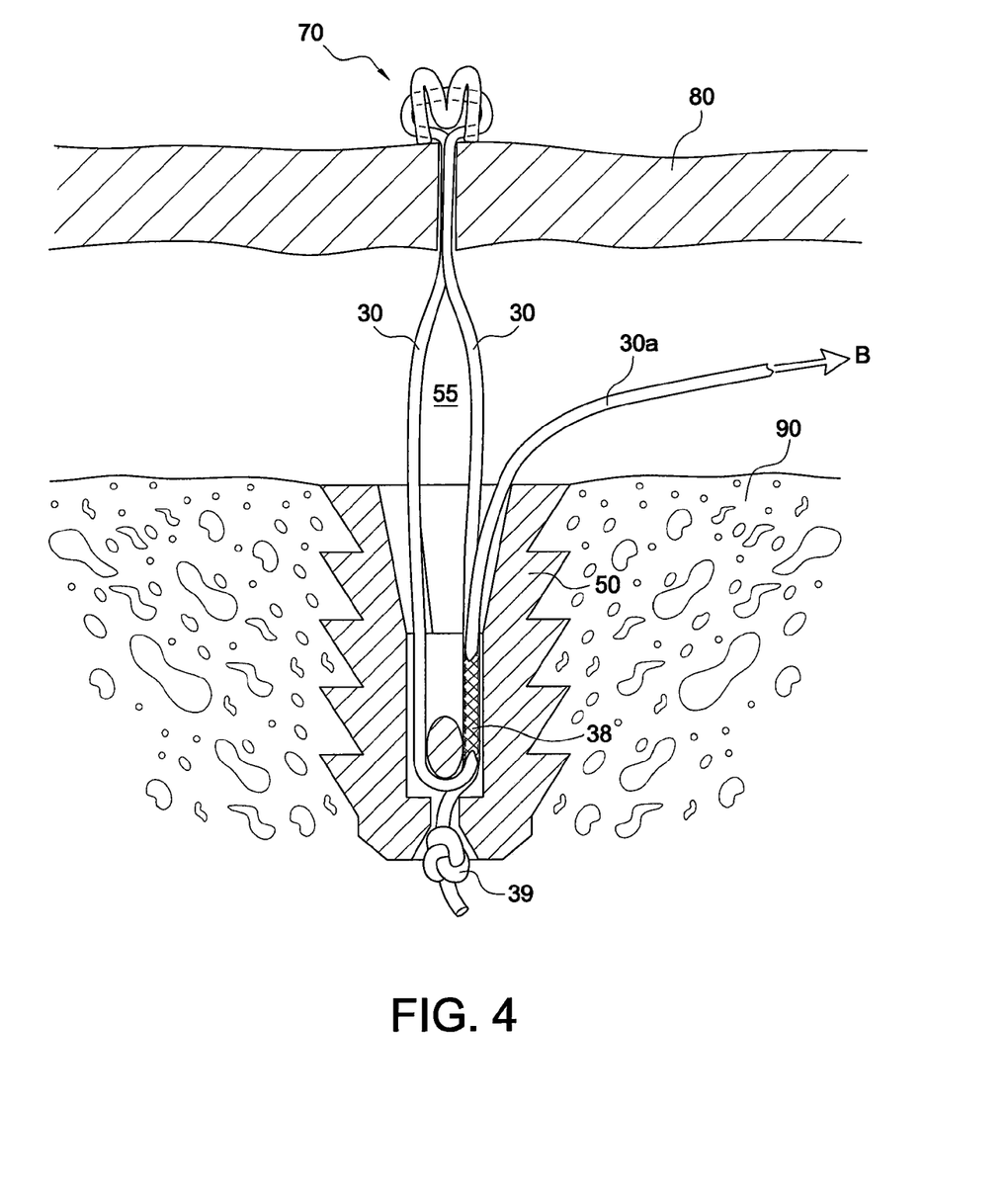
Figure 5:
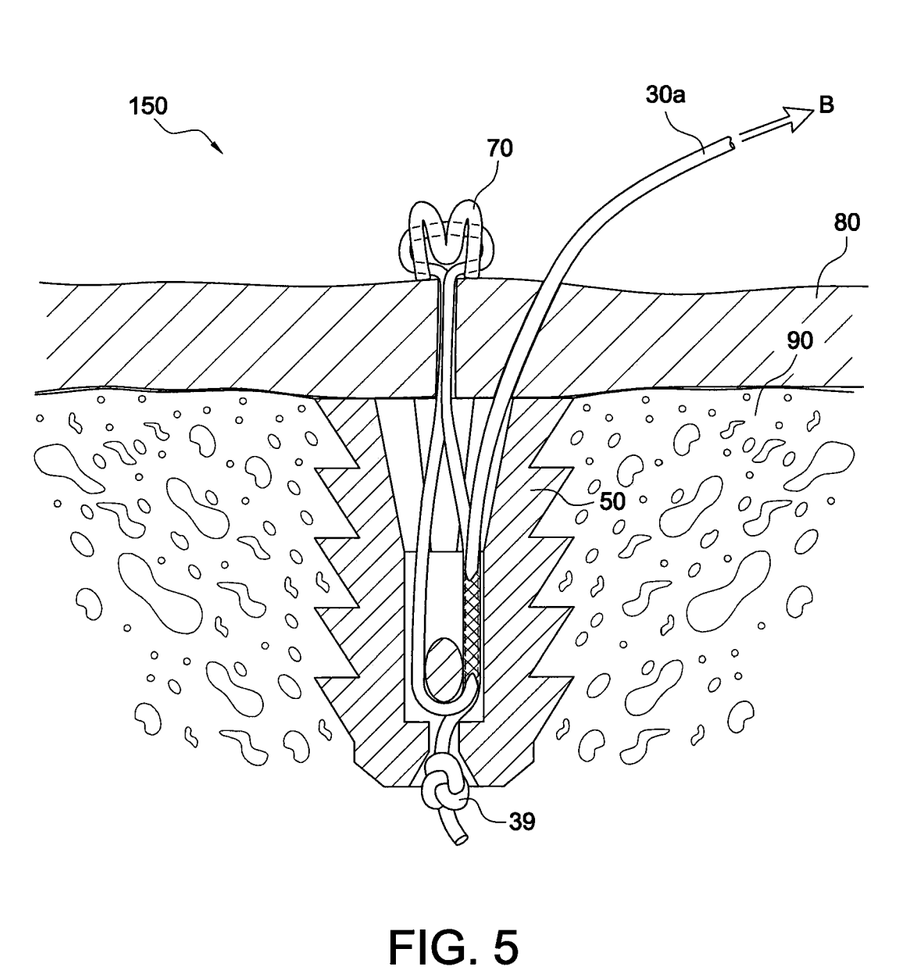

Reference is now made to FIG. 4. As the tensioning limb 30*a* is pulled in the direction of arrow B (which is different from the direction of arrow A), the suture slides through the cinching mechanism 38 (splice region 38) and flexible material 70 secures on the opposite side of the second tissue 80. In an exemplary-only embodiment, the direction of arrow B is about perpendicular to the direction of arrow A.

The tensioning limb 30*a* is pulled until the second tissue 80 is compressed against the first tissue 90 (FIG. 5), or at least until the distance between the first and second tissues is reduced, as desired. The cinching mechanism 38 will lock the suture in place and the flexible material 70 bunches up and holds the second tissue 80 to the first tissue 90 without sliding back through the bone/tissue. The tensioning limb 30*a* can be cut and repair 150 is complete.

Figure 6:
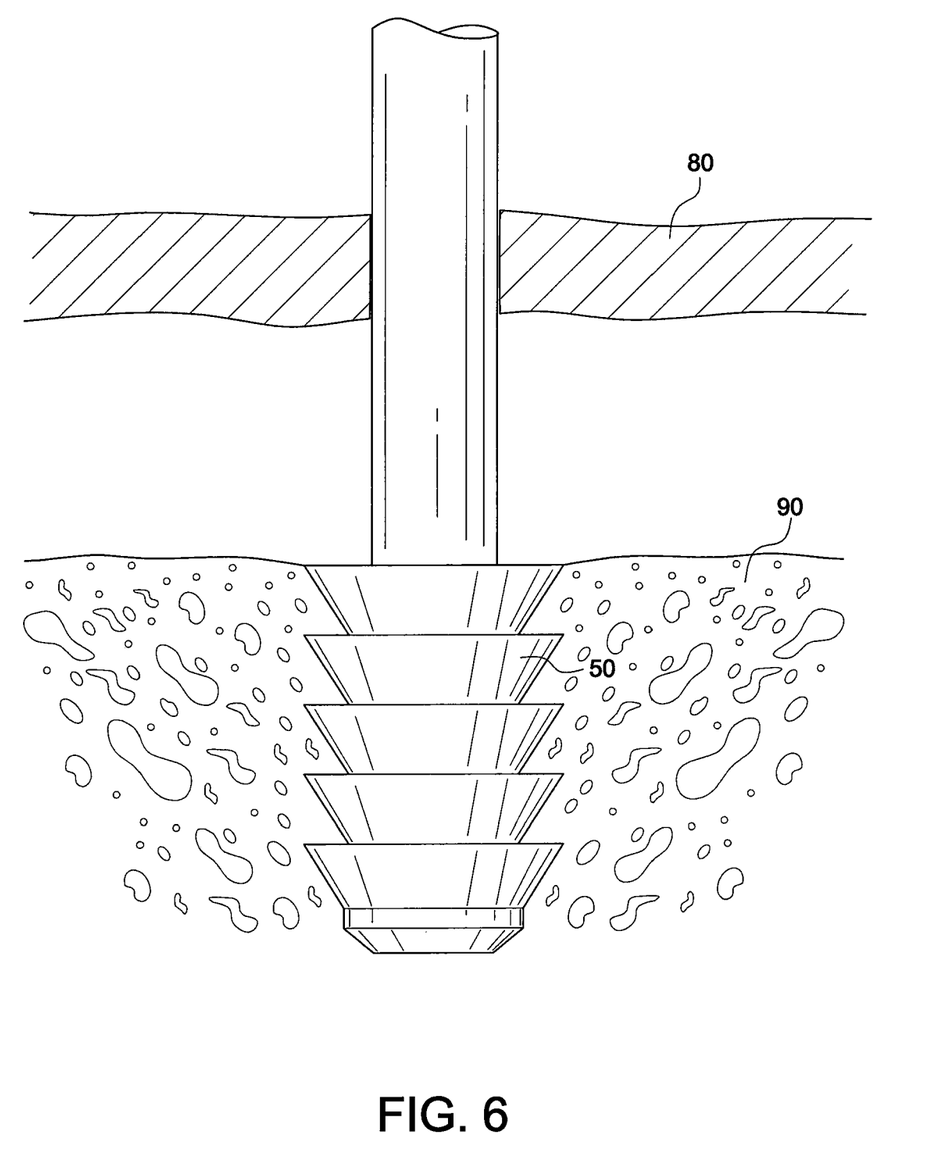
FIGS. 6 and 7 illustrate subsequent steps of a method of tissue repair using a tensionable knotless anchor according to another exemplary embodiment of the present invention (insertion method 2).
Figure 7:
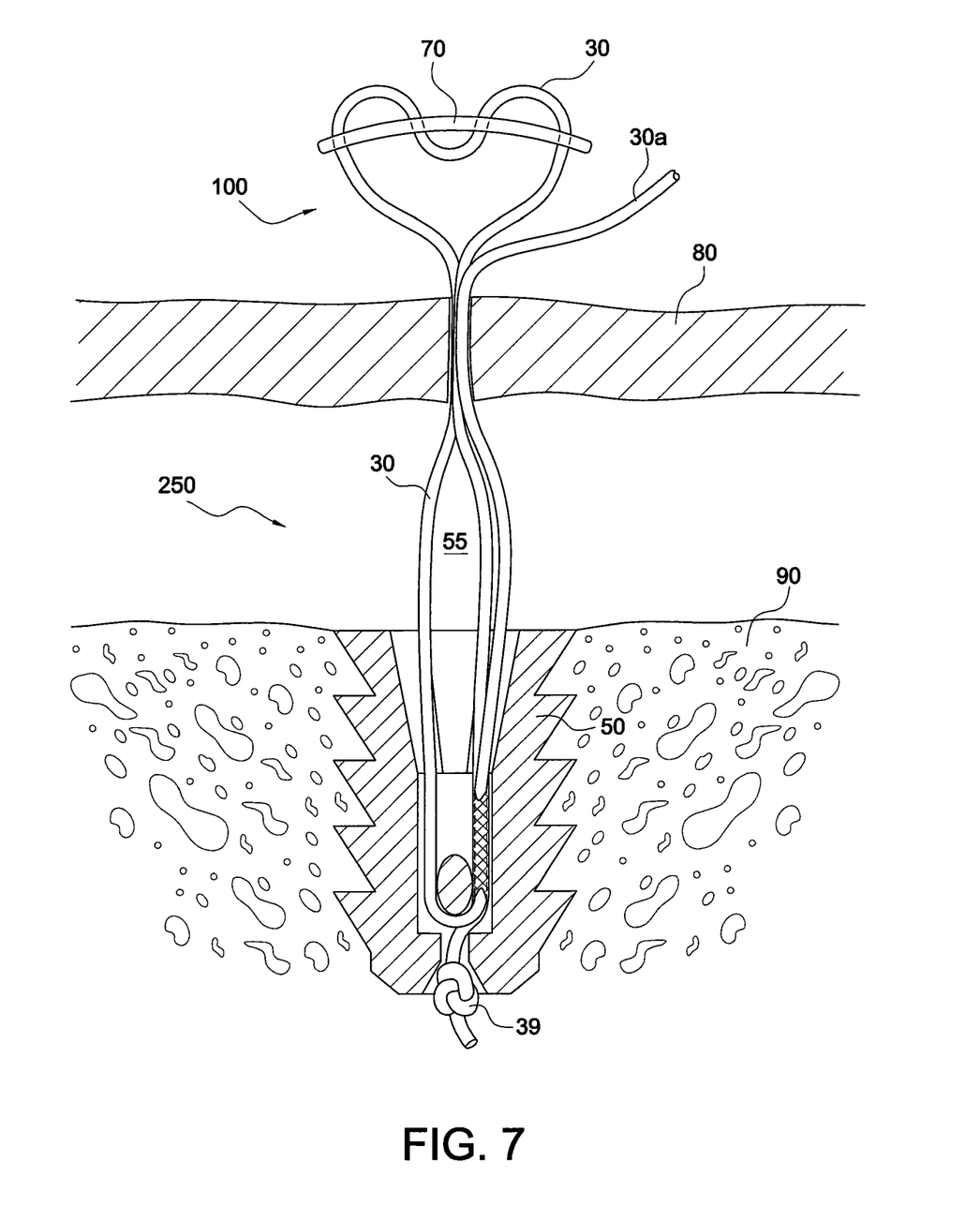

FIGS. 6 and 7 illustrate exemplary steps of another method of fixation of tissue to tissue (for example, bone to soft tissue, soft tissue to soft tissue, or bone to bone) according to the present invention. The suture anchor can be inserted directly through the second tissue 80 (second substrate or bone/soft tissue 80) and into opposing first tissue 90 (first substrate or bone/soft tissue 90), as shown in FIG. 6. This insertion step helps eliminate the need to pass the construct using the passing suture 72.

After the anchor 50 is inserted through both substrates 80, 90, the implant 100 is in place and the tensioning limb 30*a* can be pulled to bunch the material 70 and reduce the construct together, to achieve repair 250 (shown in FIG. 7).

The first tissue or substrate 90 may be bone or soft tissue such as ligament, tendon, graft, etc., or combinations thereof. The second tissue or substrate 80 may be bone or soft tissue such as ligament, tendon, graft, etc., or combinations thereof. The first tissue 90 may be similar to, or different from, the second tissue 80.

The flexible strand 30 may be a high-strength suture, such as an ultrahigh molecular weight polyethylene (UHMWPE) suture which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE. Typically the suture will be UHWMPE suture without a core to permit ease of splicing.

The flexible strands may also be formed of a stiff material, or combination of stiff and flexible materials, depending on the intended application. The strands may be also coated and/or provided in different colors. The knotless anchors of the present invention can be used with any type of flexible material or suture that forms a splice and a loop.

The materials employed for the formation of the flexible material 70 may be any natural or synthetic material, or combinations of these materials. In an exemplary-only and non-limiting embodiment, the flexible material 70 is formed of loosely braided ultrahigh molecular weight polyethylene (UHMWPE) suture. The flexible material 70 may be also formed of suture tape such as FiberTape® as disclosed in U.S. Pat. No. 7,892,256, the disclosure of which is incorporated by reference in its entirety herewith, or of ArthroFlex® which is an acellular dermal extracellular matrix (which retains its growth factors, native collagen scaffold, and elastin) intended for supplemental support and covering for soft tissue repair, among many others. As noted above, the flexible material 70 may have various forms and geometries (for example, rectangular or square, among many others) that allow flexible strand 30 to attach thereto (either in a fixed or modular manner). If desired, the flexible material 70 may be provided with a coating and/or may have a color different from the color of the flexible strand 30 to aid in discerning these structures during surgery.

The suture construct 100 (reconstruction system 100) could be utilized for multiple indications such as, for example, fracture repairs and ligament/tendon repairs such as AC joint reconstruction, syndesmosis reconstruction, quad/patellar tendon rupture repair, hallux-valgus repair, and any other tendon/ligament/bone repair. The reconstruction system 100 detailed above may be also employed in conjunction with additional various knotted and/or knotless fixation devices (or combination of such knotted and knotless fixation devices), such as PushLock® anchors and/or SwiveLock® anchors to secure, for example, a medial row on rotator cuff repairs.

An exemplary method of attaching first tissue to second tissue with surgical construct 100 of the present invention comprises inter alia the steps of: (i) providing a surgical construct 100 comprising a knotless fixation device 50 (for example, an anchor) pre-loaded with a tensionable construct 99, the tensionable construct 99 consisting of a flexible strand 30 (for example, suture) extending through the body of the fixation device, the flexible strand comprising a knotted fixed end 39 (or an insert molded end), a free end 30a, and a splice 38 with a spliced adjustable loop 55, the splice 38 being located within the body of the fixation device and the spliced adjustable loop 55 having an adjustable length/perimeter, the spliced adjustable loop 55 of the tensionable construct being pre-built with an additional flexible material 70 (bunching suture/material 70) attached to the spliced adjustable loop 55, the flexible material 70 being configured to being pulled for passage through the second tissue and for bunching up (i.e., changing its initial overall length to a second smaller overall length); (ii) inserting the fixation device 50 (with the pre-assembled or pre-loaded construct 99) into a first tissue 90 (for example, bone); (iii) passing the flexible material 70 attached to the strand 30 through a second tissue 80 to be fixated (or reattached) to the first tissue 90; (iv) positioning the flexible material 70 on a surface (for example, top surface) of the second tissue 80; and (v) pulling on the free end 30a of the flexible strand 30 to reduce the perimeter of the spliced adjustable loop 55 and to cause the flexible material 70 to bunch up on the surface of the second tissue 80, and to allow the first tissue 90 to achieve the desired location relative to the second tissue 80 upon proper tensioning of the final construct 150.

Anchor 50 may be a screw-in anchor or a push-in style anchor. Exemplary knotless anchors 50 may be formed of metal, biocompatible plastic such as PEEK or a bioabsorbable PLLA material. The anchors may be provided with a socket at the distal end (such as socket 19 of the anchor 50) configured to securely engage a tip of a driver. The socket of the anchor may have any shape adapted to receive a driver tip for pushing the anchors, for example, tap-in or screw-in style anchors. Tensionable knotless anchors 50 may be made of one or more pieces, or may be provided as integrated devices.

As detailed above, anchor 50 may have a body that is solid and cannulated. However, anchor 50 may be also a soft anchor, i.e., with a body soft anchors include a body formed of various soft materials (including, but not limited to, suture) and provided in various shapes and configurations that confer the anchors the ability to be easily inserted within bone tunnels or sockets and be bunched up within the bone tunnels or sockets. An exemplary soft anchor is Arthrex knotless FiberTak® suture anchor which is an "all-suture" soft-tissue fixation device with an expandable push-in design that is constructed from a hollow braid of polyester. An UHMWPE suture construct is assembled through the hollow braid coupled with a nitinol passing wire. The soft anchor may be provided preloaded on a disposable inserter. Details of knotless soft anchors are also set forth in U.S. Patent Application Publication No. 2014/0052178 entitled "Self-Cinching Soft Anchors" and U.S. Patent Application Publication No. 2014/0052179 entitled "Soft Anchors with Soft Eyelets," the disclosures of both of which are incorporated by reference in their entireties herein.

The knotless suture constructs and systems of the present invention are used in conjunction with any knotless fixation devices which are pre-loaded with a flexible strand forming a splice within or outside the body of the fixation device. The fixation devices may be any of swivel and/or screw-in suture anchors and/or push-in suture anchors (such as a two-piece Arthrex PushLock® anchor, disclosed in U.S. Pat. No. 7,329,272, or an Arthrex SwiveLock® anchor, disclosed in U.S. Pat. No. 8,012,174, the disclosures of which are incorporated in their entirety herewith). The fixation devices may be also any anchors, implants or screws (such as interference screws or tenodesis screws) or any fixation element that allows attachment/fixation of the knotless suture construct to bone. The fixation devices/implants may have various sizes (various diameters and/or lengths) and may be formed of biocompatible materials such as PEEK, biocomposite materials, metals and/or metal alloys, or combination of such materials, among others. The fixation devices may be unitary or may be multiple-piece constructs.

The flexible strand 30 may be a high-strength suture, such as an ultrahigh molecular weight polyethylene (UHMWPE) suture without a core which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material.

The knotless suture constructs also include sutures that are spliced—at least in part—in a manner similar to an Arthrex ACL TightRope®, such as disclosed in U.S. Pat. Nos. 8,439,976 and 8,460,379, the disclosures of which are incorporated by reference herein.

The anchor assembly of the present invention advantageously minimizes suture handling and management. The use of knotless anchors (such as push-in or screw-in type anchors) also provides secure fixation of the suture construct—the secure suture construct results from the suture being pushed into a hole and held tightly by anchors. The suture assembly employed in conjunction with the knotless anchors also allows for knotless tensioning of the tissue (rotator cuff) after the plurality of knotless anchors have been implanted.

In the embodiments detailed above, suture is used with the knotless anchors to fix tissue to bone. However, the knotless anchors of the present invention can be used with any type of flexible material or suture that forms a splice and a loop. In yet additional embodiments, any combination of suture and suture tape may be employed, depending on the characteristics of the specific surgical repair and/or as desired.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention.

What is claimed is:

1. A method of tissue repair, comprising the steps of: providing a surgical device comprising a fixation device and a flexible construct extending through the fixation device, the flexible construct comprising a flexible strand with a splice formed within the flexible strand, an adjustable loop having an adjustable perimeter, a free end, a fixed end, and a flexible material attached to the adjustable loop;
    installing the fixation device into a first tissue;
    passing the flexible strand with the attached flexible material through a second tissue after installing the fixation device into the first tissue to secure the flexible material to the second tissue;
    pulling on the free end to bunch up the flexible material and provide tensioning of the second tissue relative to the first tissue; and
    subsequently reducing a distance between the first and second tissues.

2. The method of claim 1, further comprising the steps of:
    pre-loading the flexible construct onto the fixation device;
    securing the fixation device to a driver;
    inserting the fixation device into a hole in the first tissue; and
    pulling on the free end to tension the construct.

3. The method of claim 1, wherein the fixation device is a knotless anchor.

4. The method of claim 1, wherein the flexible strand is a suture formed of ultrahigh molecular weight polyethylene.

5. The method of claim 1, wherein the splice is formed within the fixation device and the fixed end is a knot.

6. The method of claim 1, wherein the flexible material is a suture, suture tape, suture chain, textile, mesh or netting.

7. The method of claim 1, further comprising the step of attaching a passing suture to the flexible member to pull the suture with the attached flexible material through the second tissue.

8. The method of claim 1, wherein
    the first tissue is bone; and
    the second tissue is soft tissue.

9. A method of attaching tissue to bone using an anchor assembly including a driver and an anchor, the anchor comprising: an anchor body having a distal end, a proximal end, a longitudinal axis, and a flexible construct pre-loaded within the anchor body, the flexible construct including a suture with a flexible material slidingly attached to the suture and also with a suture passing instrument attached to the suture; the method comprising the steps of:
    providing the anchor pre-loaded with the suture having the attached flexible material by extending the suture within a cannulation of the anchor, the suture being secured by a knot at a most distal end of the anchor;
    pulling the suture passing instrument to allow the suture to pass through itself, within the anchor body, and to form a splice and an adjustable suture loop, the flexible material being attached to the adjustable suture loop;
    removing the suture passing instrument and installing the anchor pre-loaded with suture into a first tissue with the driver;
    removing the driver;
    passing the suture with the attached flexible material through a second tissue after installing the anchor into the first tissue, to secure the flexible material to the second tissue to be fixated; and
    pulling on a free end of the suture to bunch up the flexible material and approximate the second tissue to the first tissue.

10. The method of claim 9, further comprising the step of attaching a passing suture to the flexible member to pull the suture with the attached flexible material through the second tissue.

11. The method of claim 9, wherein
    the first tissue is bone; and
    the second tissue is soft tissue.

* * * * *